United States Patent
Humphries

(10) Patent No.: US 9,968,753 B2
(45) Date of Patent: May 15, 2018

(54) NASALLY MOUNTED RESPIRATORY MASK

(71) Applicant: Linda Humphries, Tallahassee, FL (US)

(72) Inventor: Linda Humphries, Tallahassee, FL (US)

( * ) Notice: Subject to any disclaimer, the term of this patent is extended or adjusted under 35 U.S.C. 154(b) by 563 days.

(21) Appl. No.: 14/536,952

(22) Filed: Nov. 10, 2014

(65) Prior Publication Data

US 2015/0359988 A1    Dec. 17, 2015

Related U.S. Application Data

(63) Continuation-in-part of application No. 14/304,553, filed on Jun. 13, 2014, now abandoned.

(51) Int. Cl.
    *A61M 16/06*       (2006.01)
(52) U.S. Cl.
    CPC .... *A61M 16/0666* (2013.01); *A61M 16/0683* (2013.01)
(58) Field of Classification Search
    CPC .......... A61M 16/0666; A61M 16/0672; A61M 16/0677; A61M 16/0683; A61M 2016/0661
    See application file for complete search history.

(56) References Cited

U.S. PATENT DOCUMENTS

| | | | |
|---|---|---|---|
| 7,357,136 B2 | 4/2008 | Ho | |
| 7,931,026 B2 | 4/2011 | Ho | |
| 8,286,636 B2 | 10/2012 | Gunaratnam | |
| 8,905,031 B2 * | 12/2014 | Barlow | A61M 16/0666 128/206.25 |
| 2004/0244799 A1 | 12/2004 | Landis | |
| 2009/0107508 A1 | 4/2009 | Brambilla | |
| 2009/0151729 A1 * | 6/2009 | Judson | A61M 16/0666 128/207.13 |
| 2012/0111332 A1 * | 5/2012 | Gusky | A61M 16/0666 128/205.25 |
| 2014/0083427 A1 * | 3/2014 | Andrews | A61M 16/06 128/205.25 |

* cited by examiner

*Primary Examiner* — Lynne Anderson
(74) *Attorney, Agent, or Firm* — J. Wiley Horton; Adrienne C. Love

(57) ABSTRACT

A novel gas delivery mask and associated method of use. A main mask body mounts features intended to deliver pressurized gas to a user's nostrils. A base provided. Two nostril inserts are attached to the base (either directly or through other components). The nostril inserts deliver gas to the user's nostrils. A separate sealing structure surrounds the two nostril inserts. This sealing structure includes a channel connected (directly or indirectly) to the mask and a removable soft seal placed in the channel. The soft seal is made of a pliable material that provides a gas seal and some mild adhesive properties. The mild adhesive properties allow the material to stick to both the channel and the user's skin.

20 Claims, 22 Drawing Sheets

NASALLY MOUNTED RESPIRATORY MASK

CROSS-REFERENCES TO RELATED APPLICATIONS

This non-provisional application is a continuation-in-part of U.S. application Ser. No. 14/304,553. The prior application was filed on Jun. 13, 2014. The parent application listed the same inventor.

STATEMENT REGARDING FEDERALLY SPONSORED RESEARCH OR DEVELOPMENT

Not applicable

MICROFICHE APPENDIX

Not Applicable

BACKGROUND OF THE INVENTION

1. Field of the Invention

This invention relates to the field of gas delivery masks. More specifically, the present invention comprises a mask that fits comfortably over a user's head and face in order to maintain an open airway in the respiratory system of the user. The mask is suitable for use in a continuous positive airway pressure system.

2. Description of the Related Art

A continuous positive airway pressure ("CPAP") system is used in order to keep a user's airway open in situations where the user's body is incapable of this task. A CPAP system typically includes a CPAP machine, plastic tubing, a mask, and sometimes a humidifier. The CPAP machine contains a series of filters, a motor, a fan, and other components. The motor and fan assembly pumps ambient air into the CPAP machine. Typically, that air travels through at least one filter. In some cases, the CPAP machine contains a humidifier or is connected to one. After moisture is added, the air travels through plastic tubing to the gas delivery mask. The mask may fit over the user's nose and mouth or fit into or over the user's nostrils. By sealing the passageway of the air from the CPAP machine to the user's lungs, the CPAP machine can maintain a constant pressure within the user's lungs that is greater than the ambient pressure. (Here, the system is the users lungs, airway, mask, tube, and CPAP machine.) The pressure maintained in the system provides a continuous expanding force on the user's airway, thereby sustaining an open airway.

There are multiple applications for a CPAP machine. Oftentimes, a CPAP machine is used to assist a patient who has respiratory or heart problems. This includes preterm infants with underdeveloped lungs and other patients having respiratory emergencies either in a hospital or in an ambulance. Although CPAP machines are now very common in intensive care units for such emergencies, the most common use of a CPAP machine is to alleviate sleep apnea.

Sleep apnea affects the quality of life of many individuals. Someone suffering from sleep apnea is constantly awoken during the night due to the airway closing while the patient is asleep. This leads to many symptoms including loud snoring, sore or dry throat, sleepiness during the day, forgetfulness, and drastic mood changes. A person suffering from sleep apnea is constantly drowsy because he or she is constantly being awoken during the night. In addition, athletes or other individuals have issues gaining or losing weight because the natural sleep cycle is interrupted.

A CPAP machine and mask can be used to maintain an open airway for a user, which allows the user to sleep without being constantly awoken by the closed airway. Unfortunately, sleeping with a mask over one's face can be uncomfortable. In addition, a typical gas delivery mask places a significant amount of force on the user's cheek bones that can eventually cause jaw displacement, cheek deformation, and facial nerve damage. In addition, many gas delivery masks apply significant pressure to the face near the cheekbone. This pressure applied to the cheeks can cut off circulation below the eyes, thereby reducing blood flow to the corners of the eyes, as well as some facial nerves. Straps used to secure such masks can reduce blood flow to the area above the eyes and the outside corner of the eyes. In some cases, the blood flow is almost completely cut off to the eyes. While this is dangerous for any patient, it is extremely risky for patients with eye diseases or disorders. These issues may cause users to discontinue use of the CPAP machine and mask, which causes the symptoms to continue. Either the patient discontinues use or continues to use the mask which can cause other long term damage. Therefore, finding a comfortable mask for a user is important in order to treat his or her disorder.

FIG. 1 shows prior art CPAP system 10, which is used for treating sleep apnea. CPAP system 10 includes CPAP machine 12, ventilation conduit 14, and prior art gas delivery mask 23. CPAP machine 12 includes ventilation unit 18 and humidifier unit 20. Ventilation unit 18 draws air from the ambient environment through air intake 22. That air is pulled through several filters (not shown) by means of a fan and motor assembly (also, not shown). The air is then pumped through humidifier unit 20 in order to increase the moisture in the air. Often patients have issues with an irritated or dry throat when the air is not humidified so some units include a humidifier. Once the air contains a sufficient amount of moisture (this is typically adjusted by the user), air is forced through ventilation conduit 14. Ventilation conduit 14 is attached to gas delivery mask 23, which is attached to the face of the user.

FIG. 2 shows a prior art full face gas delivery mask 23. In order to keep full face mask 23 fastened to the user's face 68, heavy duty straps 25 are attached to full face gas delivery mask 23. Straps 25 fasten behind the user's head 70, as shown in the figure. The reader will note that there are many techniques to fasten straps 25 in order to retain full face mask 23 attached to user's face 68. For example, full face mask 23 may fasten behind the head using VELCRO. The reader will also note that many different configurations of straps can be used as well. The mask configuration illustrated in the figure shows a very common type of mask. One important aspect discussed briefly in the preceding text is the impact the straps have on the user. Reduction of blood circulation to the eyes was discussed, but there are other complications as well. For example, there is typically a strap that wraps around the user's head, over the forehead, and just above the eyes. This strap can reduce circulation to the brain causing compromised cerebral blood flow—oftentimes a more serious complication than the reason for using the mask.

There are four primary disadvantages to using a full face gas delivery mask. First, straps 25 are necessarily heavy duty in order maintain the position of mask 23 on user's face 68. Second, the interaction between lip 27 and user's face 70 is preferably sealed in order to maintain pressure in the user's lungs and airway. In order for that seal to remain intact, straps 25 should be relatively tight. The tightness of straps 25 and the relatively firm material of mask 23 often cause discomfort for the user. Straps 25 and lip 27 oftentimes press against user's face 68 in a manner that not only causes discomfort, but can cause nerve damage, temporary paralysis of the face, and other complications. In fact, full face mask 23 causes such discomfort that many users discontinue sleep apnea treatment after a very short time.

Third, individuals with an oddly shaped facial structure, beards and other facial hair often have issues maintaining pressure in the lungs and airway because the face 68 and lip 27 cannot maintain a seal due to the interference of the hair or facial structure. Fourth, the tightness and position of straps 25 may cause more serious complications—such as causing (or worsening) eye disorders or disease, disturbance of cerebral blood flow, compromise of blood flow to the eye and corner of the eye, and other serious issues.

Thus, inventors have explored techniques to fabricate a gas delivery mask that is more comfortable and less intrusive. An example of this approach is found in U.S. Pat. No. 7,938,116 to Ging (2011). The Ging device provides a mask and head gear unit that includes several straps which cover much of the user's face and head. Similarly, U.S. Pat. No. 8,286,636 to Gunaratnam provides a number of straps that cover the user's head and face. In addition, the Gunaratnam device oftentimes includes rigid pieces resting against the user's face or head.

Although these devices provide a gas delivery mask and headgear to support that mask, they fail to provide a minimalist design that does not sacrifice comfort. The present invention solves this and other problems, as will be described more particularly in the following text.

BRIEF DESCRIPTION OF THE INVENTION

The present invention comprises a novel gas delivery mask and associated method of use. A main mask body mounts features intended to deliver pressurized gas to a user's nostrils. A nostril pillow is provided. Two nostril inserts are attached to the nostril pillow. The nostril inserts deliver gas to the user's nostrils. A separate sealing structure surrounds the two nostril inserts. This sealing structure includes a channel connected (directly or indirectly) to the mask and a removable soft seal placed in the channel. The soft seal is made of a pliable material that provides a gas seal and some mild adhesive properties. The mild adhesive properties allow the material to stick to both the channel and the users skin.

REFERENCE NUMERALS IN THE DRAWINGS

Figure 1:
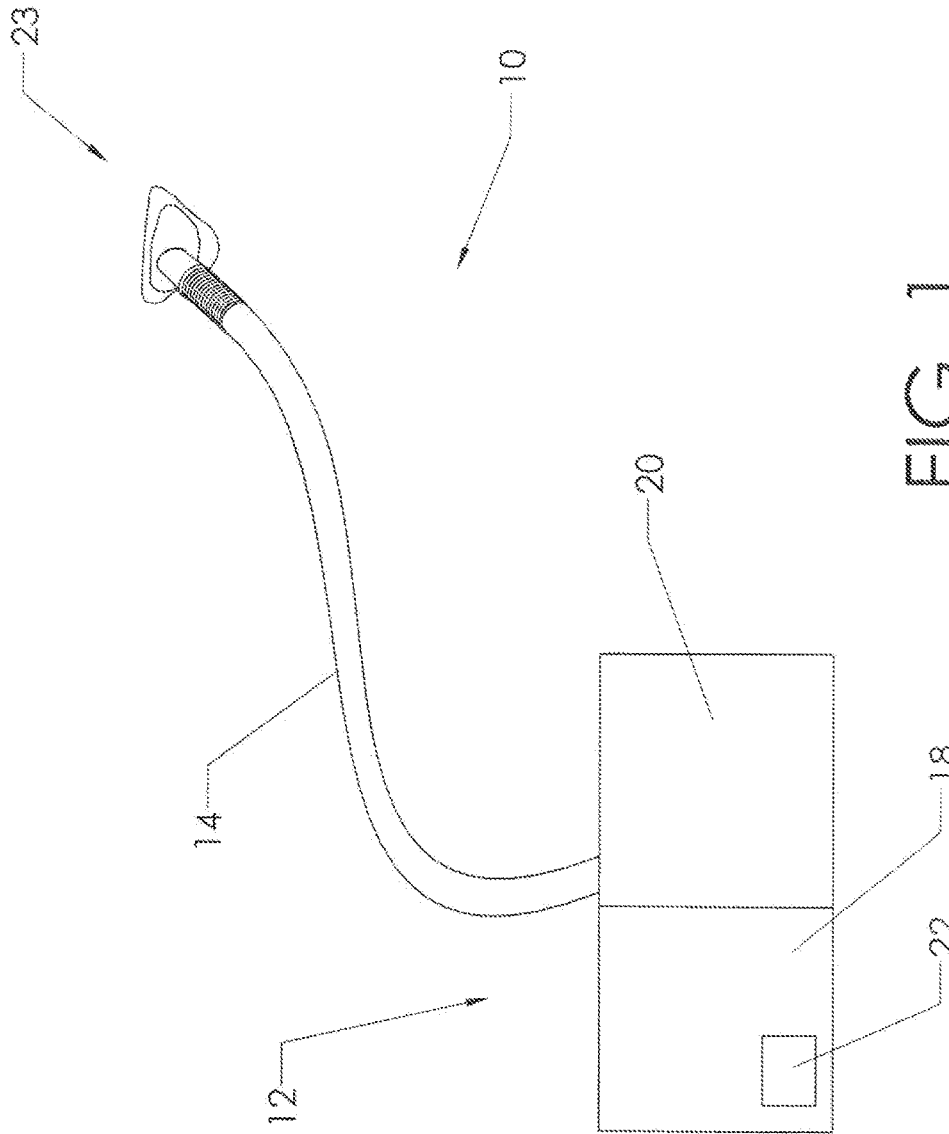
FIG. 1 is an elevation view, showing a prior art continuous positive airway pressure system attached to a prior art mask.
Figure 2:
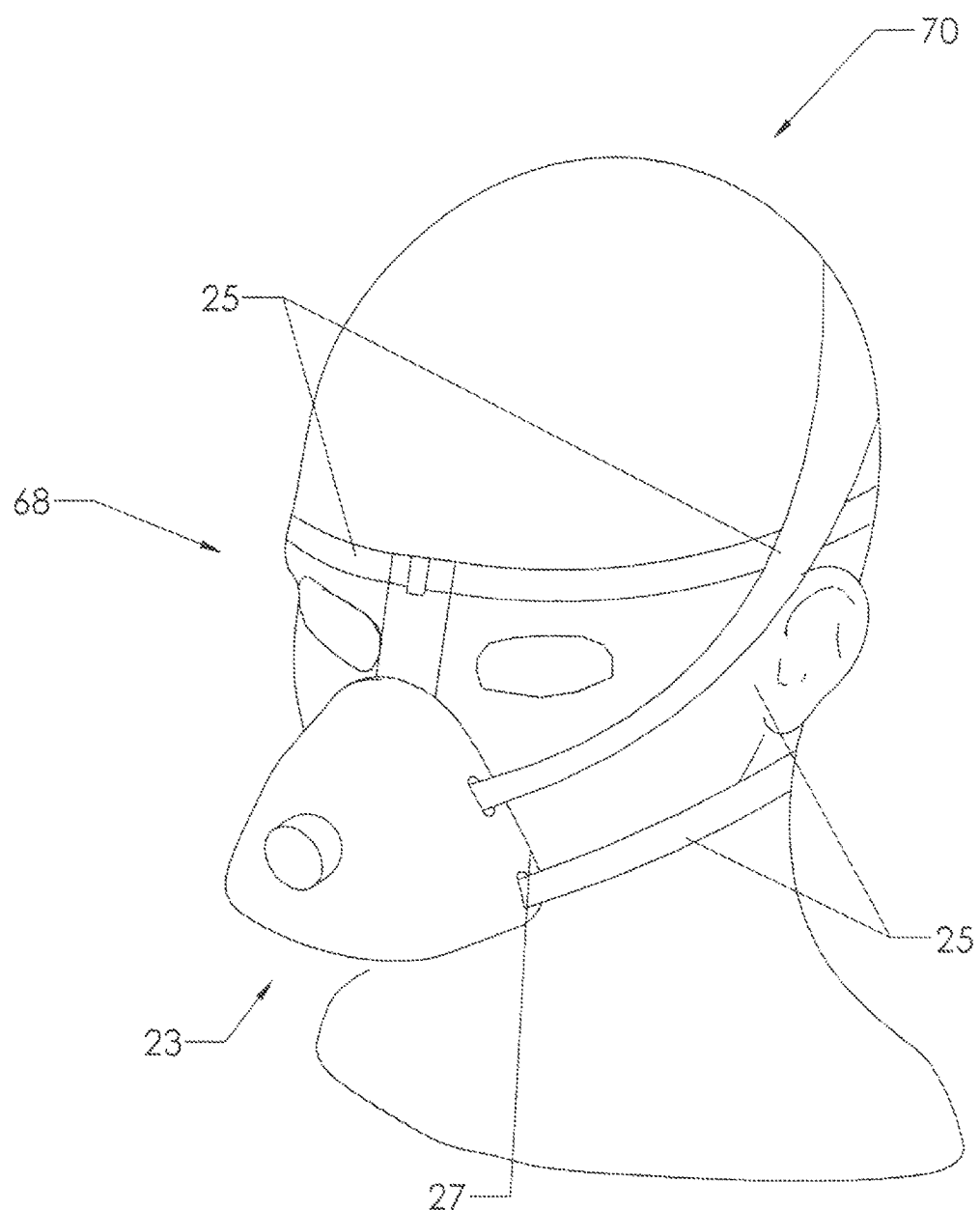
FIG. 2 is a perspective view, showing a prior art full-face mask.

10 CPAP system
12 CPAP machine
14 ventilation conduit
16 gas delivery mask
18 ventilation unit
20 humidifier unit
22 air intake
23 full face gas delivery mask
24 main mask body
25 strap
26 nostril pillow
27 lip
28 elongate member
29 base
30 lateral extreme
32 concave surface
34 main mask body opening
36 main mask body lip
38 groove
44 inner groove surface
46 Inner lip surface
48 nostril insert
50 hole
52 cushion
54 parallel surface
56 slot
58 pin
60 cap 62 fastening end
64 pivot joint
66 user
70 head of user
72 strap
74 coupling
76 side strap
78 ear of user
80 elongate member strap slot
82 strap end
84 loop
86 main mask body strap slot
88 front strap
92 second end of front strap
94 inside coupling slot
96 coupling top surface
98 outside coupling slot
100 cheekbone
102 strap cushion
104 sealing structure
106 side wall
110 nose of user
112 coupler
114 vent
116 base opening
118 snap feature
120 channel
122 soft seal

DETAILED DESCRIPTION OF THE INVENTION

The present invention provides a comfortable gas delivery mask that may be used to maintain an open airway within the respiratory system of a user by means of a CPAP system such as that shown in FIG. 1. The invention may be used in other applications as well, such as the delivery of breathing oxygen or other gasses.

Figure 3:
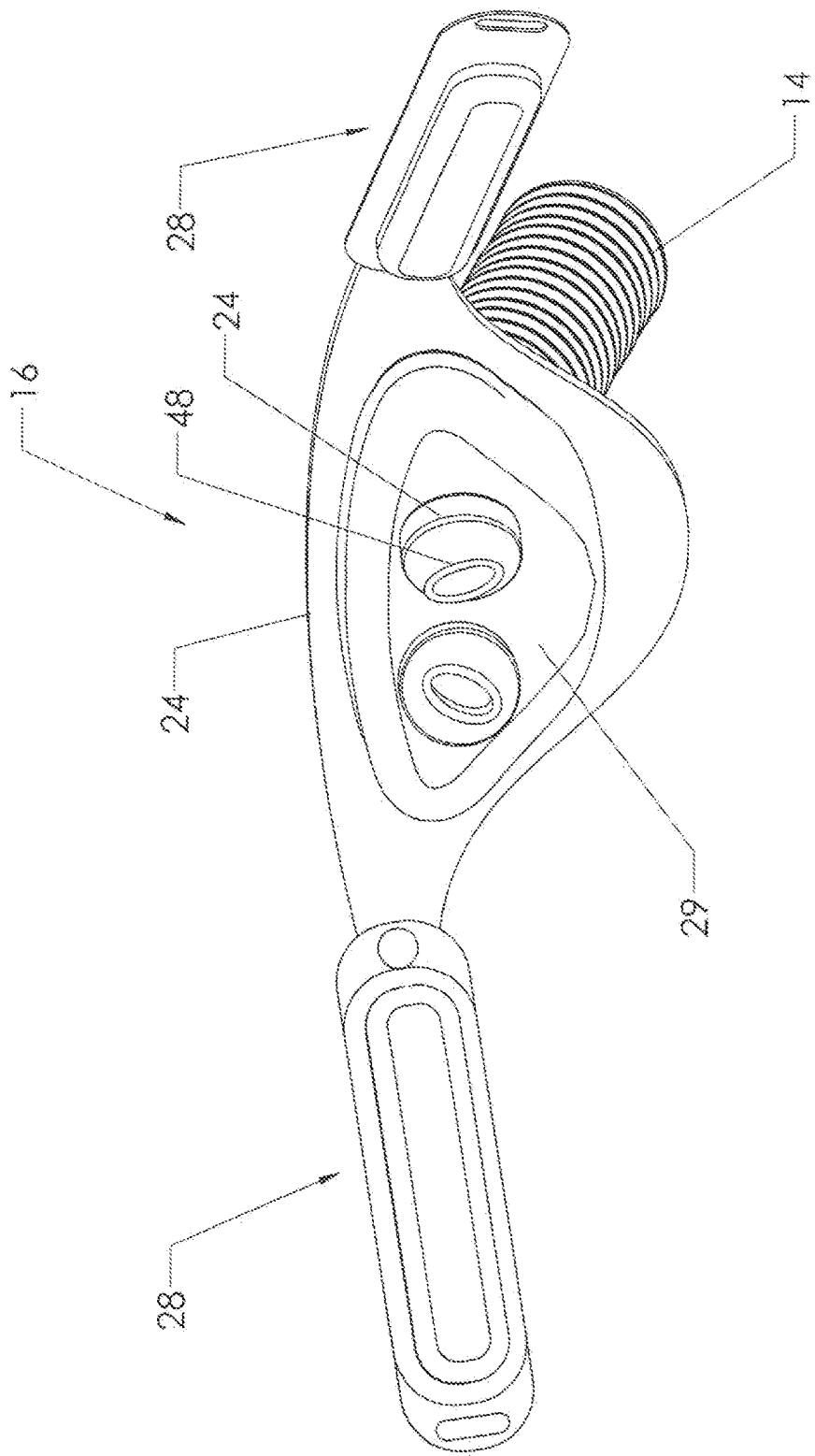
FIG. 3 is a perspective view, showing an embodiment of the inventive mask having elongate members on either side.

A CPAP system such as shown in FIG. 1 is intended for individuals who struggle to maintain an open airway independently. FIG. 3 shows a preferred embodiment that is configured for use with a CPAP machine. Gas delivery mask 16 includes main mask body 24 as a unifying structural element that links the other components together. Ventilation conduit 14 feeds pressurized air to the mask assembly. The pressurized air is fed into the user's nostrils through an assembly of nostril-interfacing components. These are base 29, nostril pillows 26, and nostril inserts 48. Each nostril insert 48 is configured to slip into a user's nostril and deliver gas through an opening in the nostril insert. Nostril pillows 26 and nostril inserts 48 are made soft and pliable so that they do not exert undue pressure on the user's nose when in position.

The mask assembly is intended to secure the nostril-interfacing components in place in a manner that allows the device to be worn comfortably for many hours, in a preferred embodiment of the invention, each component of gas delivery mask 16 is attached (directly or indirectly) to main mask body 24. Preferably, main mask body 24 is rigid enough to maintain the overall shape of the mask as it is urged toward the user's face. The reader will understand that main mask body 24 typically will have some limited flexibility. However, it is important to keep the overall integrity and structure of main mask body 24 even if it is capable of deforming easily. It should be noted that the term "rigid" in reference to main mask, body 24 should be interpreted as holding form when left undisturbed, but capable of deformation when acted upon by an outside force.

Figure 4:
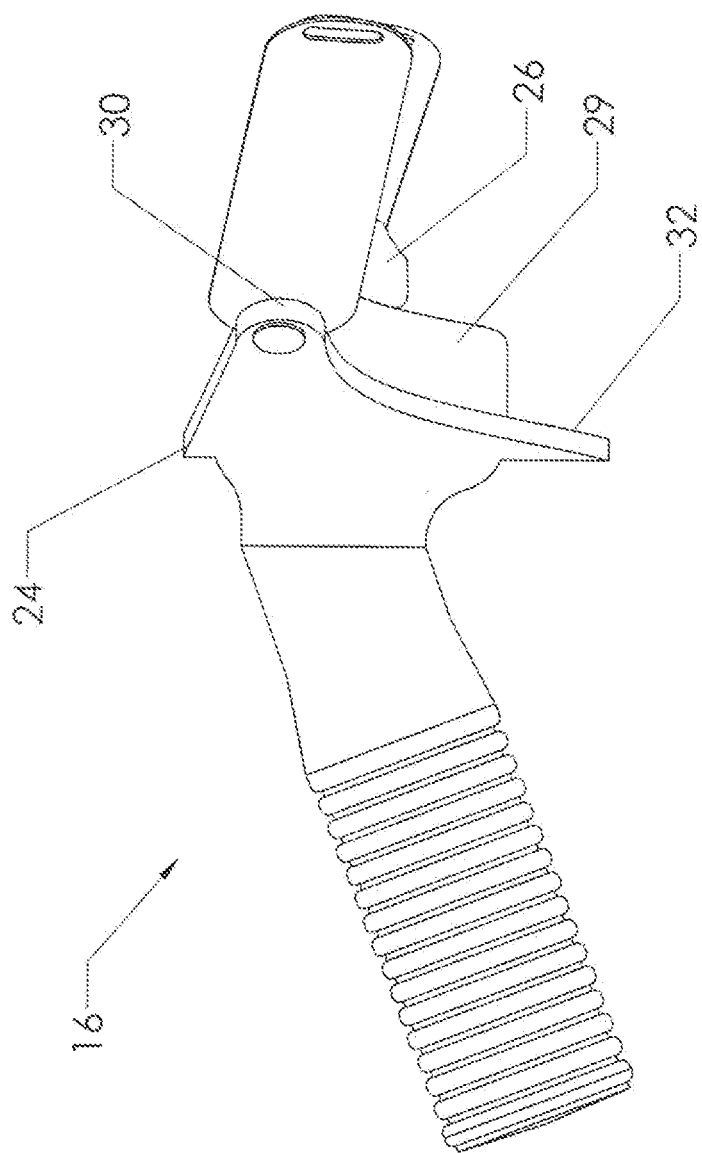
FIG. 4 is an elevation view, showing the embodiment shown of FIG. 3.

FIG. 4 shows a right elevation view of the embodiment of FIG. 3. This view shows the curvature of main mask body 24 in the lateral direction. The curvature of main mask body 24 is preferred in order to accommodate the curvature of a user's face and head. Preferably, the radius of curvature of main mask body 24 is small enough for mask 16 to contour to a user's face. However, the radius of curvature of main mask body 24 should not be so small that a portion of the main mask body actually touches the user's face. The area of most concern is lateral extreme 30 of main mask body 24 (An extreme exists at on both sides). Lateral extreme 30 could cause the user discomfort if it contacts the face of the user. Also, in the prior art, a strap connecting the mask is attached to this point and then passes around the head. The strap cuts into soft tissue proximate the cheekbones, whereas in the present invention this generally does not occur.

Gas delivery mask 16 may be made available in multiple sizes. Individuals with different sized heads and faces may require a larger or smaller sized mask. A larger sized mask may include main mask body 24 having more surface area and/or the radius of curvature of main mask body 24 increasing. One of the primary objectives of mask 16 is to provide comfort to the user so it is preferable that lateral extreme 30 does not press into the face of the user. By including multiple sizes for gas delivery mask 16, the comfort of multiple users can be taken into account.

Returning now to FIG. 3, some of the details of the nostril-interfacing components will be explained. The primary purpose of the main mask body and associated securing straps is to properly position the nostril-interfacing components so that pressurized gas is delivered to the user's nostrils. The nostril-interfacing components are base 29, nostril pillows 26 and nostril inserts 48. Each nostril pillow is a flexible and soft chamber that delivers gas to the nostril inserts. Each nostril insert is also soft and hollow. Each nostril insert is sized to slip within one of the user's nostrils.

Each nostril pillow is preferably made with bulging side walls so that, it may easily compress as the mask assembly is applied to the user's face. The nostril pillows are configured 10 retain the nostril inserts within the user's nostrils without placing excessive pressure on the downward-facing surfaces of the user's nose.

Figure 5:
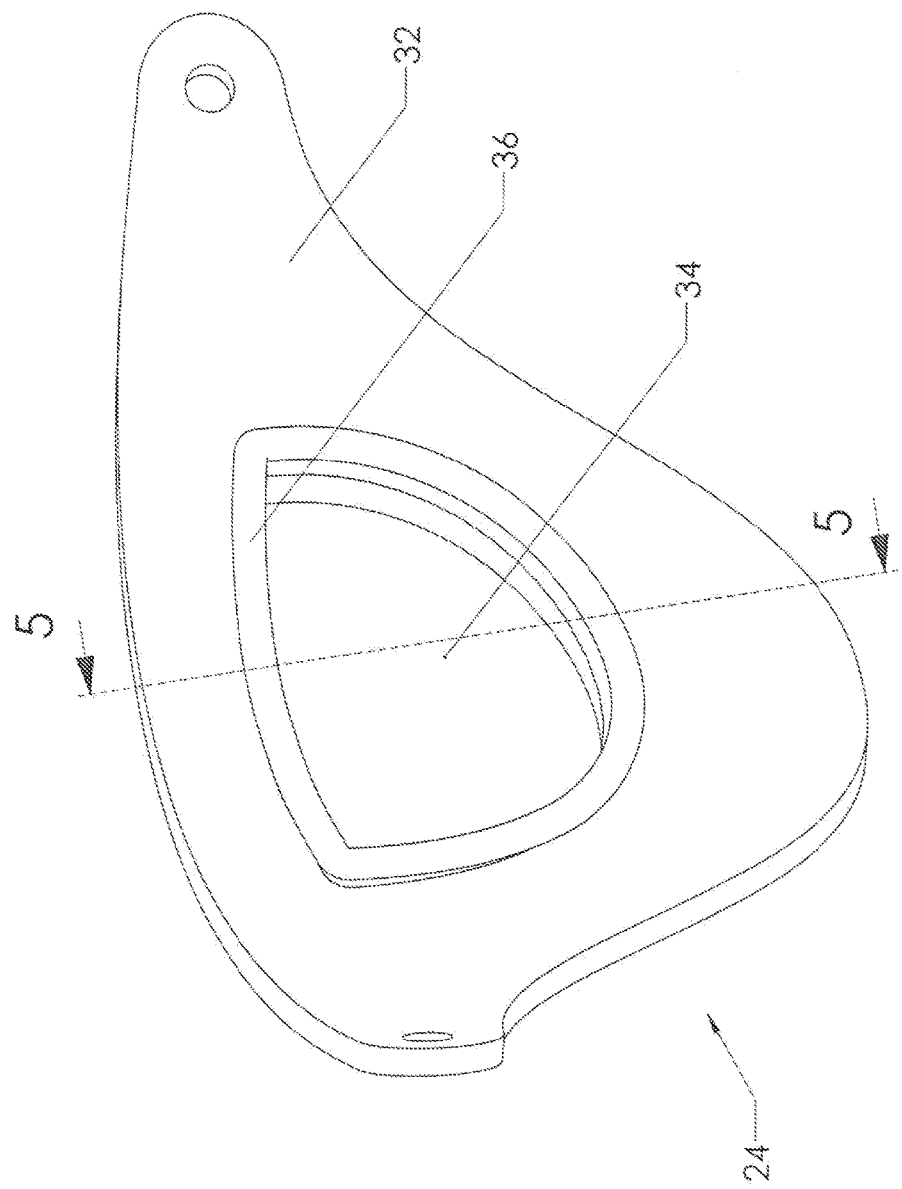
FIG. 5 is a perspective view, showing the main mask body used to connect the mask components to the securing straps.

The present invention is not limited to any particular way of attaching the nostril-interfacing components to the main mask body, but it may aid the reader's understanding to know some of the ways in which, this assembly can be created. FIGS. 5-8 show one illustrative embodiment. A perspective view of main mask body 24 is shown in FIG. 5. Main mask body 24 includes main body opening 34. Main body opening 34 is located approximately the center of main mask body 24. This opening allows air to travel through main mask body 24. Main body opening 34 is shown in a shape that is similar to the shape of main mask body 24. The reader should note that main body opening 34 can assume many forms other than the form shown. Therefore, the functionality, not the form, should drive the design of opening 34. The function of opening 34 is to allow sufficient passage of air from CPAP machine 12, or any other respiratory device, to the user. As long as this requirement is met, the shape and size of main body opening 34 has little effect on the present invention.

Main mask body 24 may include a mask body lip 36 located on concave surface 32. In addition, main mask body lip 36 is preferably located along the edges of main mask body opening 34. The lip structure may be used to secure other components to the main mask body. In some embodiments, main mask body lip 36 is used to secure nostril pillow 26 to main mask body 24.

Figure 6:
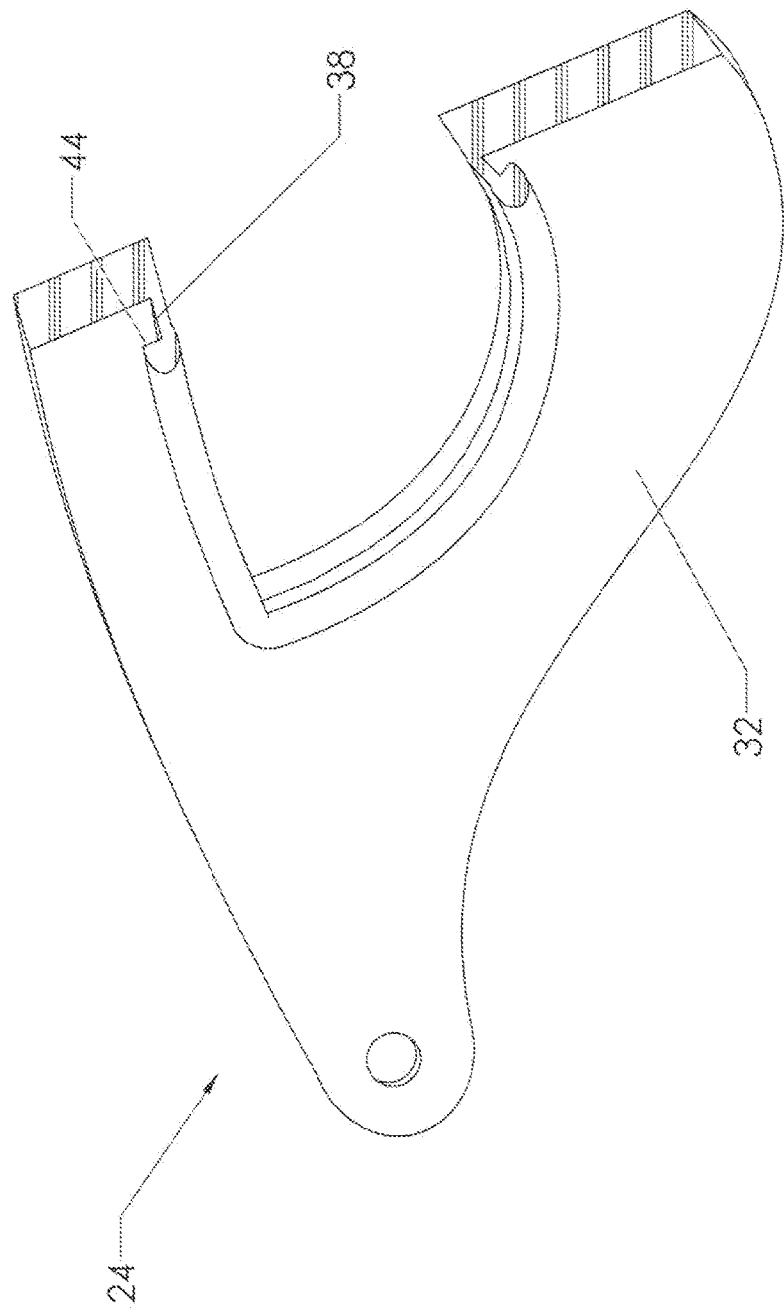
FIG. 6 is a sectional view, showing a section through the main structural member depicted in FIG. 5.

The dashed line in FIG. 5 indicates the cut line for a sectional view. That view is shown in FIG. 6. Main mask body 24 is cut along the centerline in order to show the mechanism used in this embodiment to fasten nostril pillow 26 to main mask body 24. Main mask body lip 36 includes groove 38. The reader will observe that lip 36 and groove 38 create a book shape. This hook shape creates a retainment mechanism for base 29. Base 29 includes a similar structure that allows base 29 to be securely fastened to concave surface 32.

Figure 7:
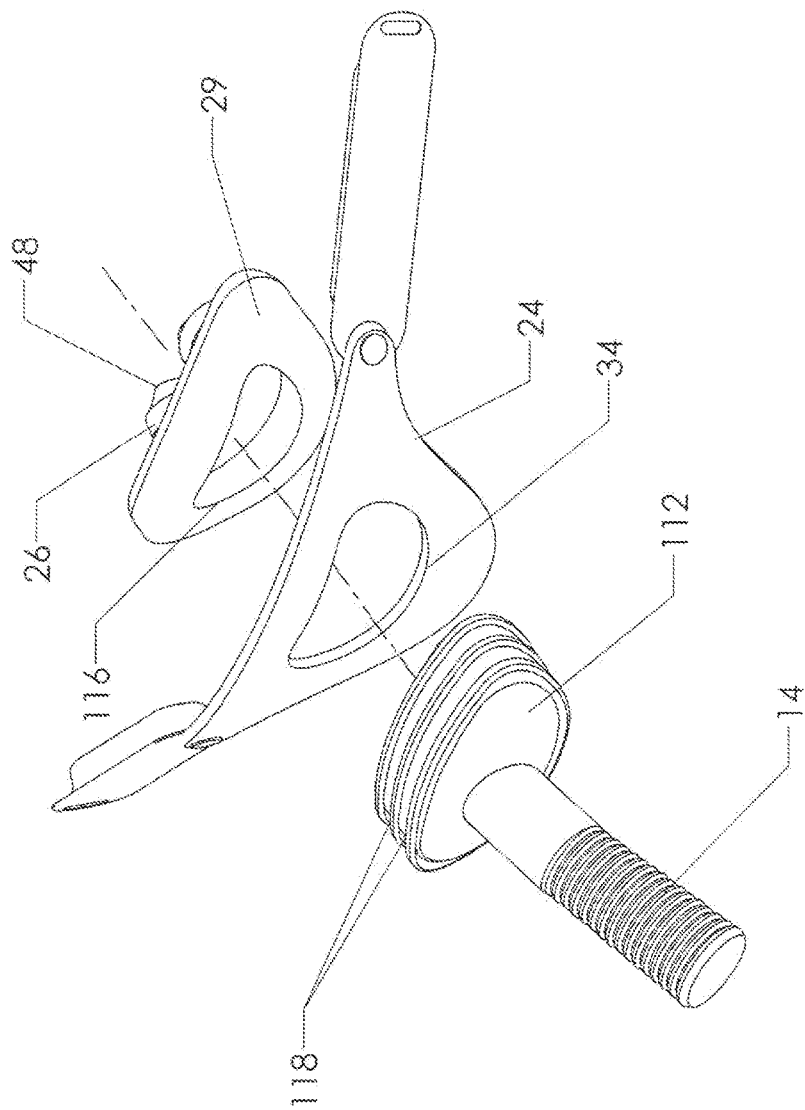
FIG. 7 is an exploded perspective view, showing the components used to connect the nostril-interfacing components to the vent conduit used to feed pressurized air.

FIG. 7 shows an exploded view of some of the separate components that are united by main mask body 24. In this embodiment the opening through the main mask body does not necessarily include a lip structure, as "snap" features on other components serve to secure the components together. Vent conduit 14 is connected to coupler 112. Coupler 112 is provided with a pair of snap features 118. The first snap feature snaps into main body opening 34 and connects coupler 112 to main mask body 24. Base opening 116 in base 29 snaps over the second snap feature on coupler 112, thereby connecting base 29 to the assembly of the coupler and the main mask body. Coupler 112 included a passage allowing gas to flow from vent conduit 14 into base 29, through nostril inserts 48, and ultimately into the user's nostrils.

Figure 8:
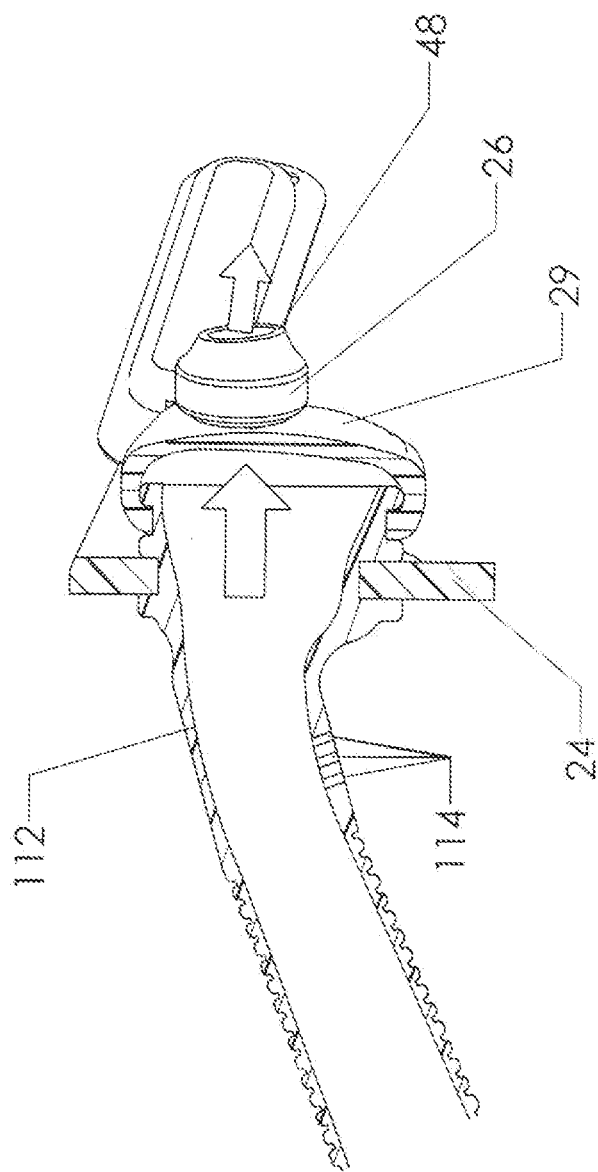
FIG. 8 is a sectional view, showing the attachment features connecting the vent conduit to the main mask body and the nostril-interfacing components.

FIG. 8 shows a sectional elevation view through the coupler, the main mask body, and the base after the assembly has been snapped together. One snap feature 118 on coupler 112 is snapped into the opening through main mask body 24. This engagement links coupler 112 to main mask body 24. The opening in base 29 snaps over the second snap feature. This combination creates an air-tight assembly (under mild pressures) that allows the flow of gas through, the coupler and ultimately through nostril pillows 26 and out nostril inserts 48—as shown by the arrows in the view.

The snap features shown are one possibility among many others. The components may also be united using adhesive, ultrasonic welding, or some other methodology. The nature of these components and how they may be fastened together is understood in the art.

Nostril pillows 26 and nostril, inserts 48 are preferably molded of soft and pliable material so that they may conform to the features of a user's face and create an adequate pressure seal. As one example, molded silicone may be used to create this assembly. The nostril inserts may be molded integrally with base 29 and nostril pillows 26 or may be molded separately and then united together using snap features or some other method.

A snap connection between the nostril-interfacing devices and the balance of the mask is advantageous in that it allows the nostril components to be easily removed from main mask body 24. This is important for cleaning and other purposes. Base 29 can also be "snapped" on and off of main mask body 24 in order to clean, replace, or service either part for any other reason.

Figure 22:
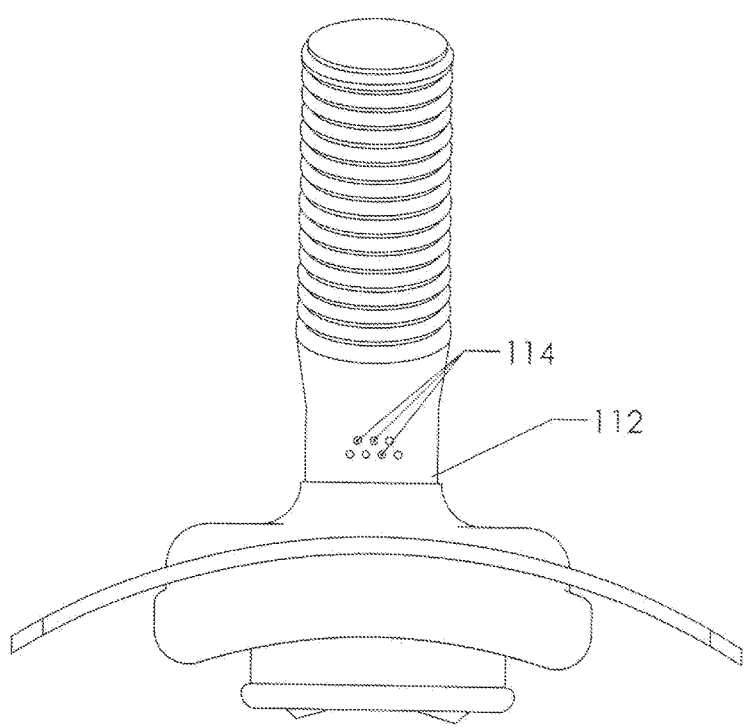
FIG. 22 is a bottom view, showing how the pressure vents on the coupler face downward.

It is common for a CPAP assembly to include vents for relieving excess pressure when the user is not inhaling. Vents 114 are provided in the downward-facing portion of coupler 112 for this purpose. These direct air downward and away from sensitive portions of the user's face. FIG. 22 shows a bottom view of the coupler and mask. The location and orientation of vents 114 may be more easily seen in this view.

As mentioned previously, the mask assembly must retain the nostril-interfacing components in the proper position for the mask to be effective. Straps are typically passed around the user's head to retain the mask assembly in position. These straps can place unwanted pressure on the user's face, and the inventive mask preferably includes features intended to address this problem. Returning to FIG. 3, the reader will observe that gas delivery mask 16 includes a pair of elongate members 28 extending from either side. These replace a portion of the prior art straps and create a much larger and softer contact interface with the user's face.

Figure 9:
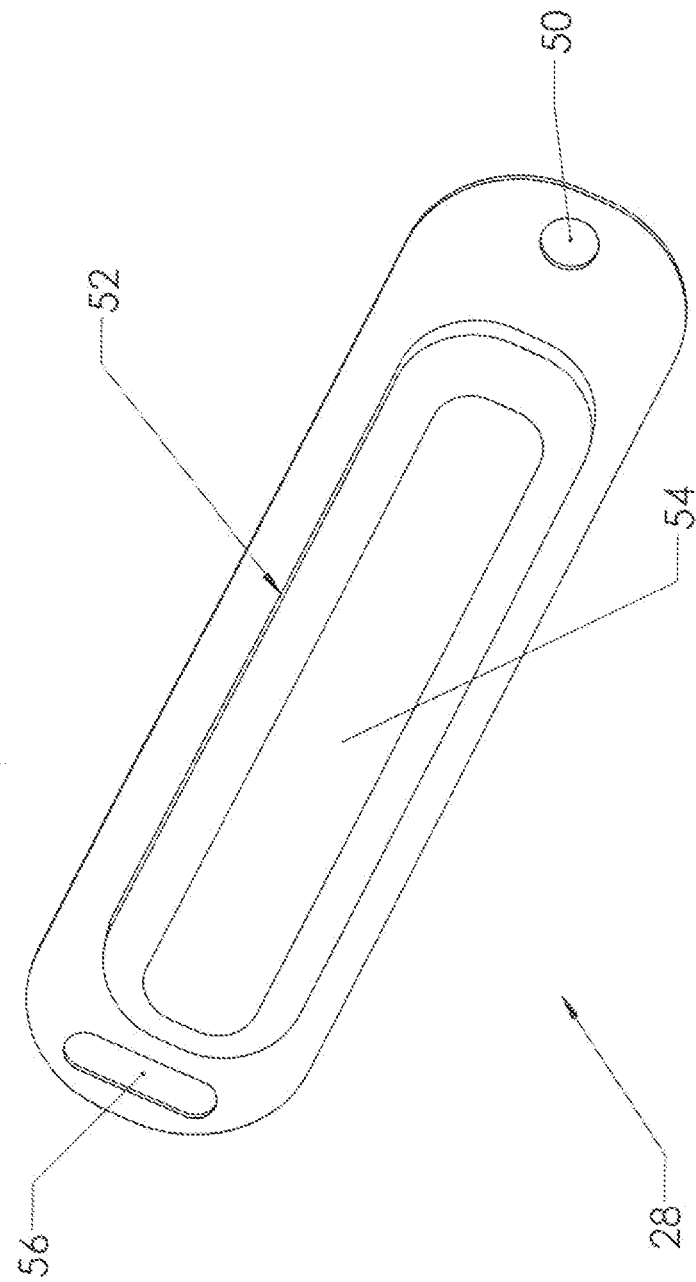
FIG. 9 is a perspective view, showing the elongate member used in the embodiment shown in FIG. 3.

One embodiment of elongate member 28 is shown in FIG. 9. Elongate member 28 includes hole 50 on one end and slot 56 on the other. Hole 50 is used to pivotally attach elongate member 28 to main mask body 24. Slot 56 is used to attach a band or other strap to elongate member 28. These connection methods are discussed further in the subsequent text. Cushion 52 extends inward from the body of elongate member 28. The cushion is preferably made of soft "gel" so that it deforms easily and conforms to the contours of the user's cheek. In this embodiment, cushion 52 includes a broad parallel surface 54. This broad surface distributes the load across a relatively large area of the user's cheek structure.

A gel cushion is preferred because it minimizes any concentration of the contact pressure. A gel cushion is soft enough to give the user comfort, while still firm enough to keep the mask from shifting. Although a gel pad is the preferred material used for cushion 52, there are other options. For example, cushion 52 can be constructed from foam, soft plastic, thick cloth, or many other materials. Furthermore, the present invention can include a combination of any of those elements such as a gel cushion that is covered in a thick fabric. This combination would reduce the friction on the face of the user while still providing the support and comfort of the gel cushion. Those familiar with the art will realize that cushion 52 (whether it is fabricated from gel or another material) distributes the force created by tightening mask 16 in a more effective manner than a simple strap. The increased force distribution is made possible because of the increased surface area and ability of cushion 52 to conform to the face of the user. Thus, the force acting upon the user's face is reduced, thereby reducing the risk of damaging nerves in the cheek and the eyes of the user.

Figure 10:
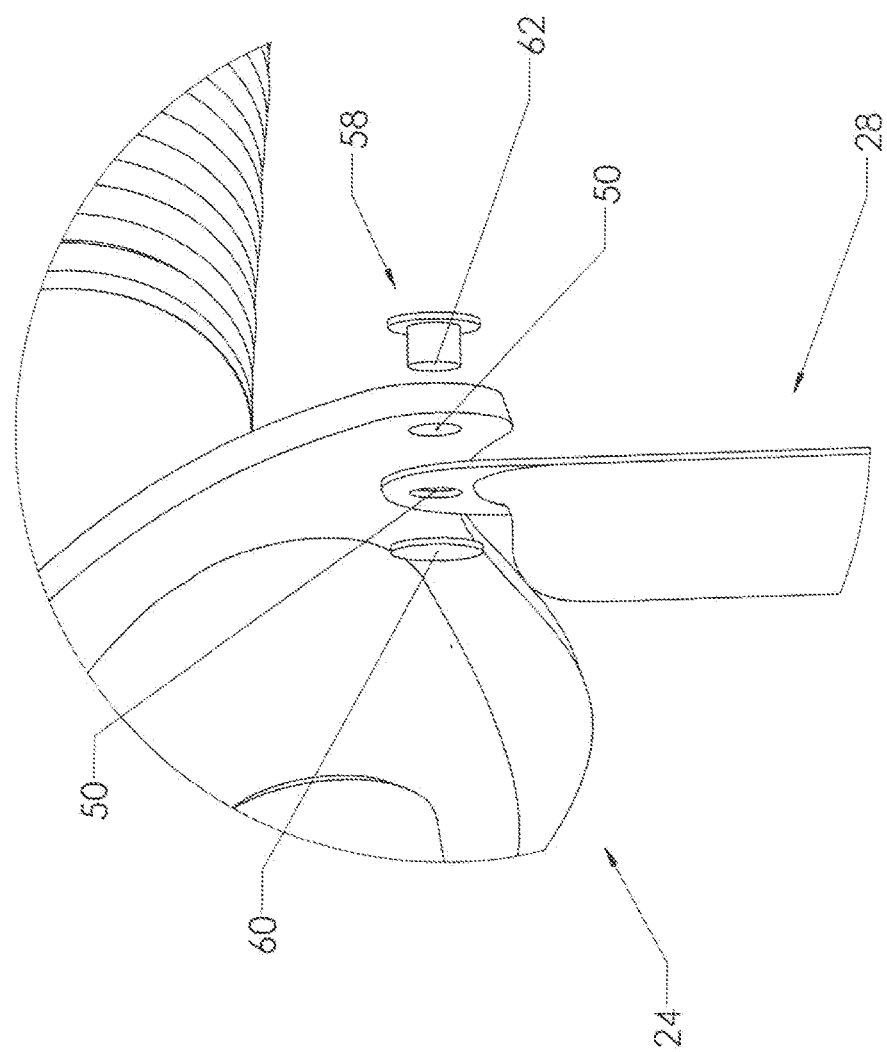
FIG. 10 is an exploded detailed view, showing one method of attachment of the elongate member to the main mask body.

FIG. 10 shows a detailed exploded view of the region of assembly for elongate member 28 and main mask body 24. Preferably, main mask body 24 includes hole 50. Pin 58 is preferably inserted into hole 50 on main mask body 24 and hole 50 on elongate member 28. After pin 58 is inserted, cap 60 is fastened to fastening end 62 thereby attaching elongate member 28 to main mask body 24. The method of fastening cap 60 to fastening end 62 can take many forms. Cap 60 can fasten to pin 58 by means of threading, press fit, snap clip, or any other suitable means. The fastening technique used to attach fastening cap 60 to fastening end 62 may be permanent or temporary. For example, if fastening end 62 and cap 60 are threaded, the user can remove cap 60 from pin 58 in order to remove elongate member 28 from main mask body 24. This is useful if the user has a need for removing elongate member 28 from the assembly to be cleaned, replaced, or for any number of reasons.

Figure 11:
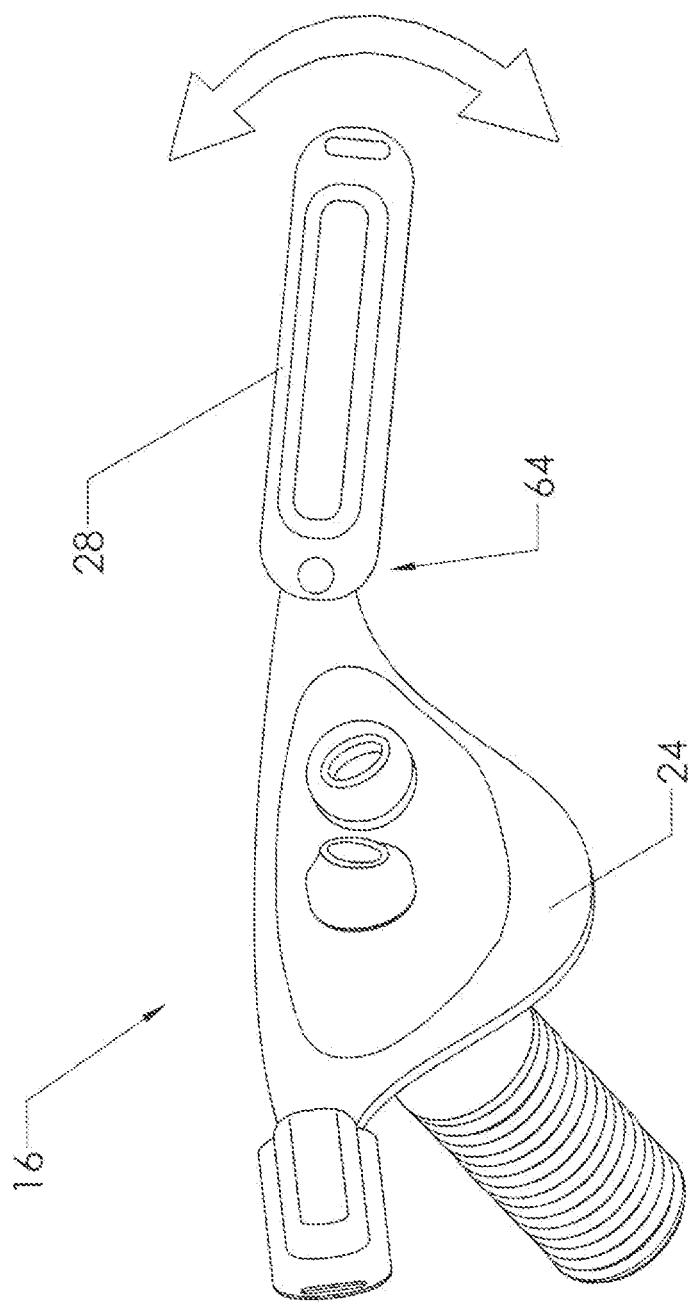
FIG. 11 is a perspective view, showing the pivotal motion of the elongate members with respect to the main mask body.

As those familiar with art will know, a pivot joint restricts translational motion while allowing rotational motion. In a preferred embodiment of mask 16, the connection of elongate member 28 and main mask body 24 is a pivot joint—as discussed in the preceding paragraph. FIG. 11 shows the advantages of using pivot joint 64 as the attachment method for main mask body 24 and elongate member 28. Elongate member 28 is capable of rotating about the axis of pivot joint 64. The rotation feature is demonstrated by the reciprocating arrow in FIG. 11. The rotating feature of gas delivery mask 16 allows the user to adjust the position of elongate member 28 on the cheek, which represents a significant advantage. The adjustment feature enables the user to adjust elongate member 28, which allows gas delivery mask 16 to fit a variety of users. By rotating about the concentric axis of hole 50, elongate member can be adjusted up or down on a user's face. The combination of multiple mask sizes and rotation of elongate member enables mask 16 to fit a variety of facial types and sizes.

In an alternate embodiment of the present invention, pivot joint 64 has a locking mechanism that allows the user to lock the angular position of elongate member 28 once the optimum position has been determined. Those familiar with the art will realize that there are several techniques that can be employed in order to lock the angular position of elongate member 28, including a push button that extends one or more protrusions that lock into corresponding holes, a push button or knob that can be pulled that engages an interlocking protrusion and slot, a twistable knob that tightens an unloaded spring or other device, or another similar approach that locks the rotational motion of elongate member 24.

Although the use of a pivot joint in order to attach elongate member 28 to main mask body 24 is demonstrated, the reader should not limit the scope of the invention to such a connection. There are many methods that can be used to attach elongate member 28 to main mask body 24 apart from a pivot joint. For example a clipping device can be used to attach the two pieces. Lateral extreme 30 could contain the receiving portion of the clip while hole 50 on elongate member 28 is replaced with the insertion piece of the clip. In addition to providing an alternative to pivot joint 64, a clip system would allow (1) the user to have a quick release to remove his or her mask and (2) the user to maintain the strap size at the same setting when the mask is removed. These advantages would allow a user who suffers from sleep apnea (and wears his or her mask every night) to quickly and easily replace and remove the mask without further adjustment.

Figure 12:
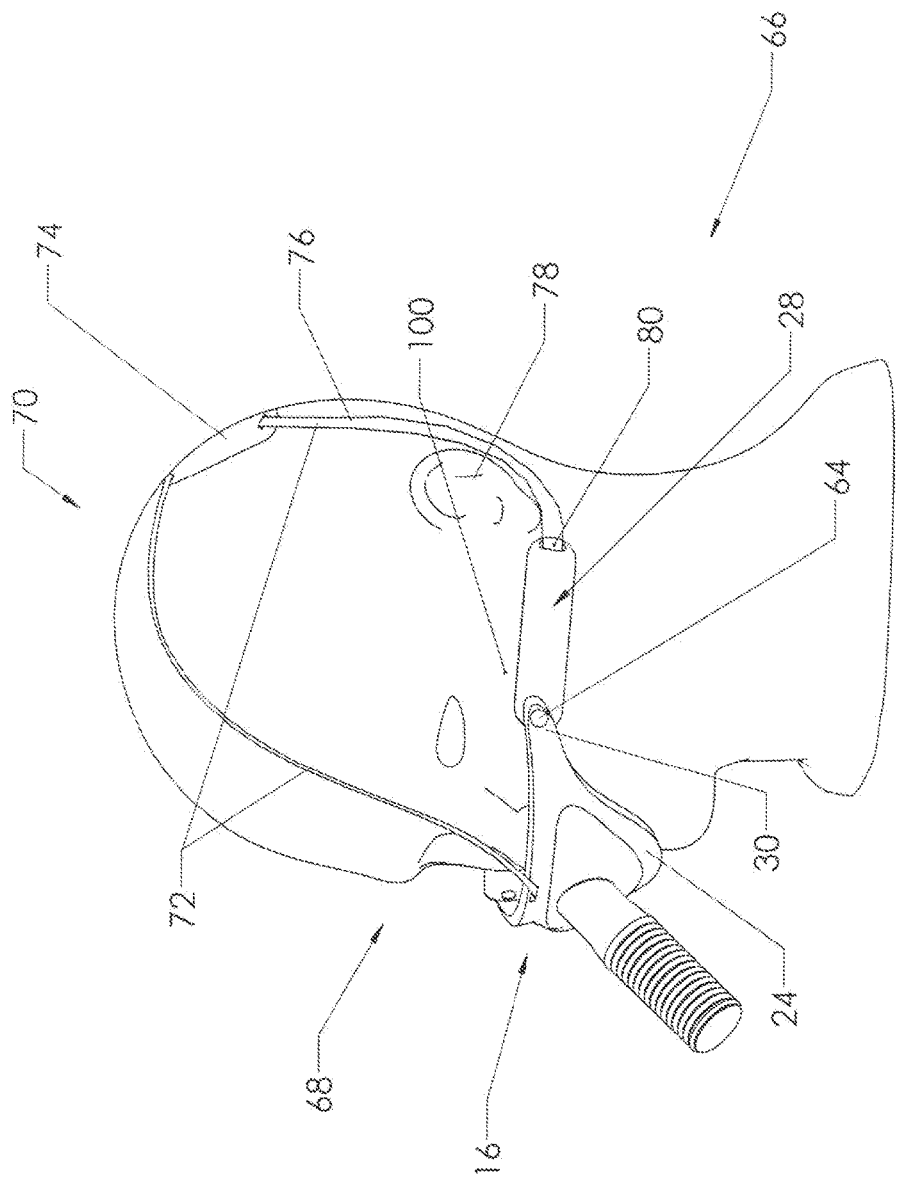
FIG. 12 is a perspective view, showing the embodiment of FIG. 3 attached to the face of a user.

FIG. 12 shows gas delivery mask 16 attached to the face of user 66. As discussed in the preceding text, the nostril-interfacing components are held in the proper position with respect to the user's nostrils (hidden in the vantage point of FIG. 12). Preferably, mask 16 is held to the lace of the user 68 by using straps 72, which fasten at the back of the user's head 70. In a preferred embodiment of the present invention, each elongate member 28 rests against a cheekbone 100. Elongate members 28 preferably act as a bridge from main mask body 24 to the start of straps 72. Preferably, cushion 52 acts a cheek pad, resting against cheekbone 100. This prevents the straps actually cutting into the user's face in the vicinity of the cheekbones. While cushion 52, or cheek pad, is described as a "gel pad" in the preceding text, in general it is preferably a soft and pliable pad covering at least a portion of the inward facing side of elongate member 28.

Figure 13:
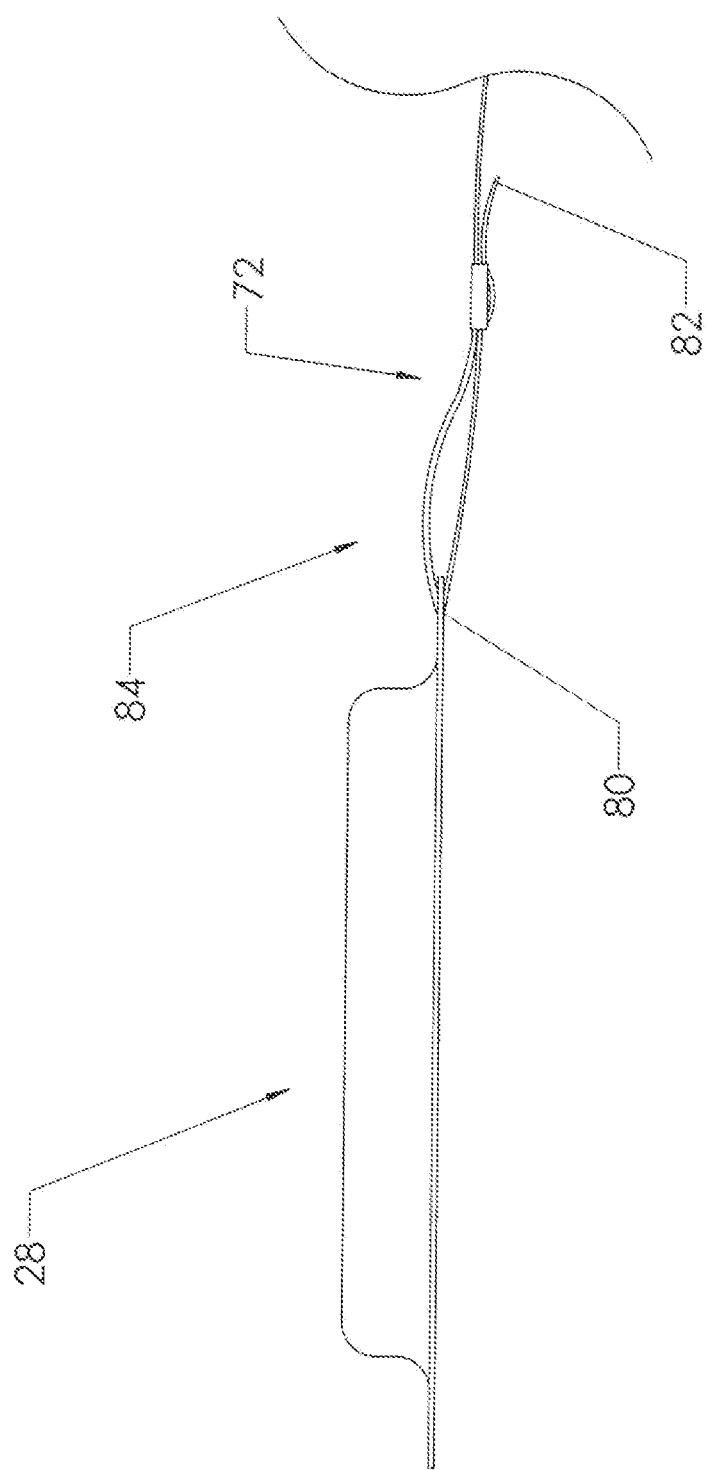
FIG. 13 is an elevation view, showing how a securing strap may be attached to the elongate member.

In the embodiment shown, gas delivery mask 16 is held to the face of the user 68 using three straps 72 and coupling 74. A side strap 76 rests under each ear 78. Each side strap 76 connects to coupling 74 (the details of this connection are discussed further in the following text) and elongate member strap slot 80. FIG. 13 shows one possible attachment method of elongate member 28 and strap 72. In order to attach strap 72 to elongate member 28, strap end 82 is inserted through elongate member strap slot 80. This forms loop 84 that secures strap 72 to elongate member 28. Then, strap end 82 is fastened to strap 72 to keep loop 84 intact. (This prevents strap end 82 from coming back through strap slot 80.) Straps 72 are preferably fabricated from an elastic material. The loop is passed through a buckle to hold it in place. The user may tighten the strap by pulling on the free end.

In another embodiment of the present invention, strap end 82 is fastened to strap 72 in a permanent manner. For example, strap end 82 can be attached to strap 72 using adhesive. The necessity for adjustment at this position in the system is limited. However, the reader should not take this as limiting the attachment method of strap end 82 to strap 72. Instead of attachment by adhesive, strap end 82 can attach using a temporary method such as VELCRO. In addition, loop 84 can be formed by tying a bow instead of attaching strap end 82 to strap 72. Thus, there are multiple techniques, permanent and temporary, in which strap end 82 can be fastened to strap 72 in order to keep strap 72 from unfastening.

Figure 14:
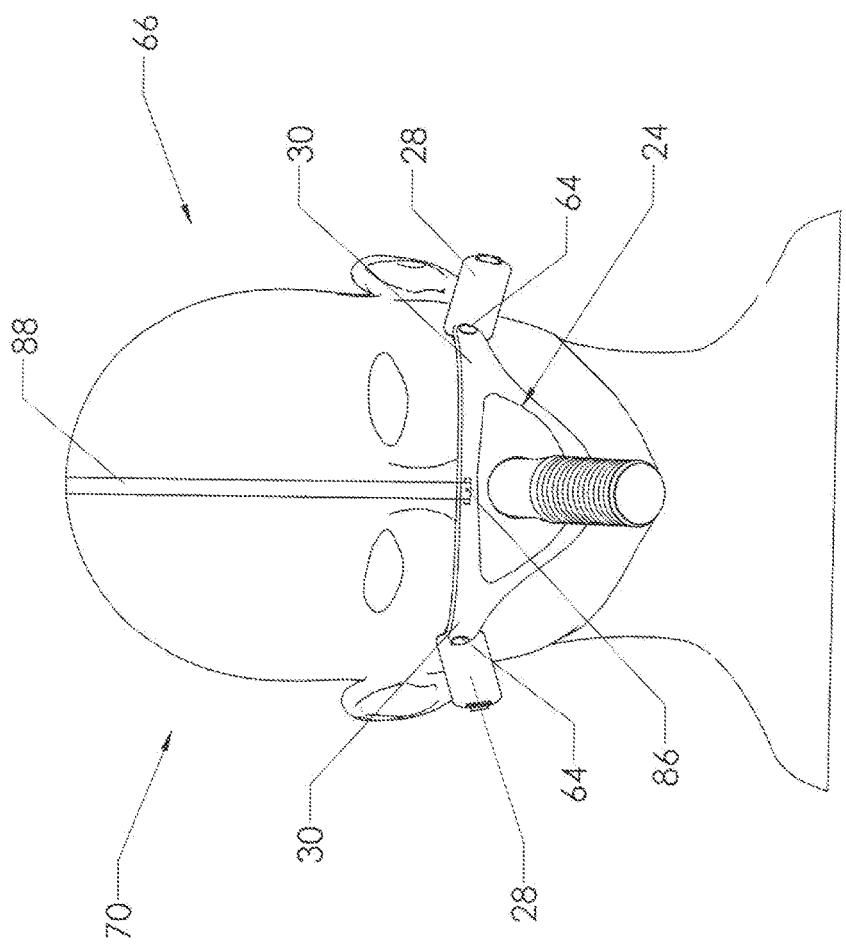
FIG. 14 is an elevation view, showing the position of the center strap on a user's head.

A front view of user 66 is shown in FIG. 14. In the figure, gas delivery mask 16 is attached to the user's face. Main mask body 24 includes main mask body strap slot 86. Front strap 88 includes a first and a second end. The first end of the front strap is connected to main mask body 24 at slot 86. This connection may include a length-adjusting feature In a preferred embodiment of the present invention, front strap 88 is located in the center of the face of the user 66. Front strap 88 travels along the nose of the user between his or her eyes. The second end of front strap 88 attaches to coupling 74 (not visible in FIG. 14) proximate the rear of the user's head. The reader will notice that the view in FIG. 14 further demonstrates how elongate members 28 rest against the user's cheekbones and prevent the straps "biting" into this area. Furthermore, the figure illustrates that the user can adjust elongate member 28 such that cushion 52 is in the most comfortable position while resting against the cheekbones.

Those skilled in the art will realize that a significant amount of the weight of gas delivery mask 16 may be supported by front strap 88 in certain cases. Thus, it is preferable that front strap 88 is constructed in a manner such that the material and thickness are adequate to support the necessary weight while maintaining optimal comfort for the user.

Figure 15:
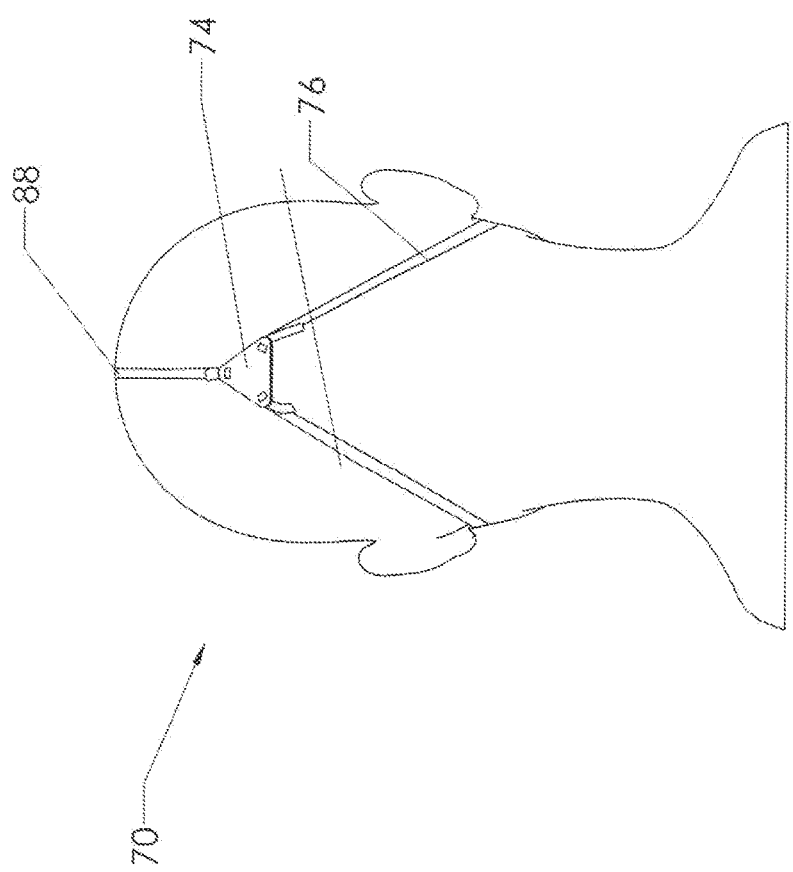
FIG. 15 is a perspective view, showing an embodiment in which a coupling positioned on the back of a user's head joins each strap attached to the gas delivery mask.

The joining of side straps 76 and front strap 88 may assume many forms. One such form is shown in FIG. 15. In the embodiment shown, front strap 88 and side straps 76 are joined behind the user's head 70 using coupling 74. Coupling 74 has a triangular profile (with filleted vertices). Each strap is attached proximate a vertex of the triangle. The method of attachment is discussed in the subsequent text. The reader will observe that the design of coupling 74 is important for the support system of this particular embodiment. The force created in front strap 88 due to the weight of mask 16 creates tension in side straps 76. The tension created in side straps 76 urges mask 16 tighter to user's face 68, which assists in keeping mask 16 in the proper position.

Another advantage of the preferred form of coupling 74 illustrated in the figures is that coupling 74 rests flat against the user's head. If a fairly flexible material is used it can even conform to the curvature of the user's head. A flat surface for the user to rest his or her head upon is preferred for the present invention. The reader will note that while coupling 74 is shown having a triangular profile with slots for joining straps 72, it may take many forms. For example, coupling 74 may simply be the three straps 72 tied together or coupling 74 can take the form of a circular piece with one central hole to which each strap 72 is tied. In addition, the two side straps 76 can be made as a singular strap that wraps around the user's head 70. This would change the form of coupling 74 as well. In this case, coupling 74 could just be front strap 88 tied to singular side strap 76.

Figure 16:
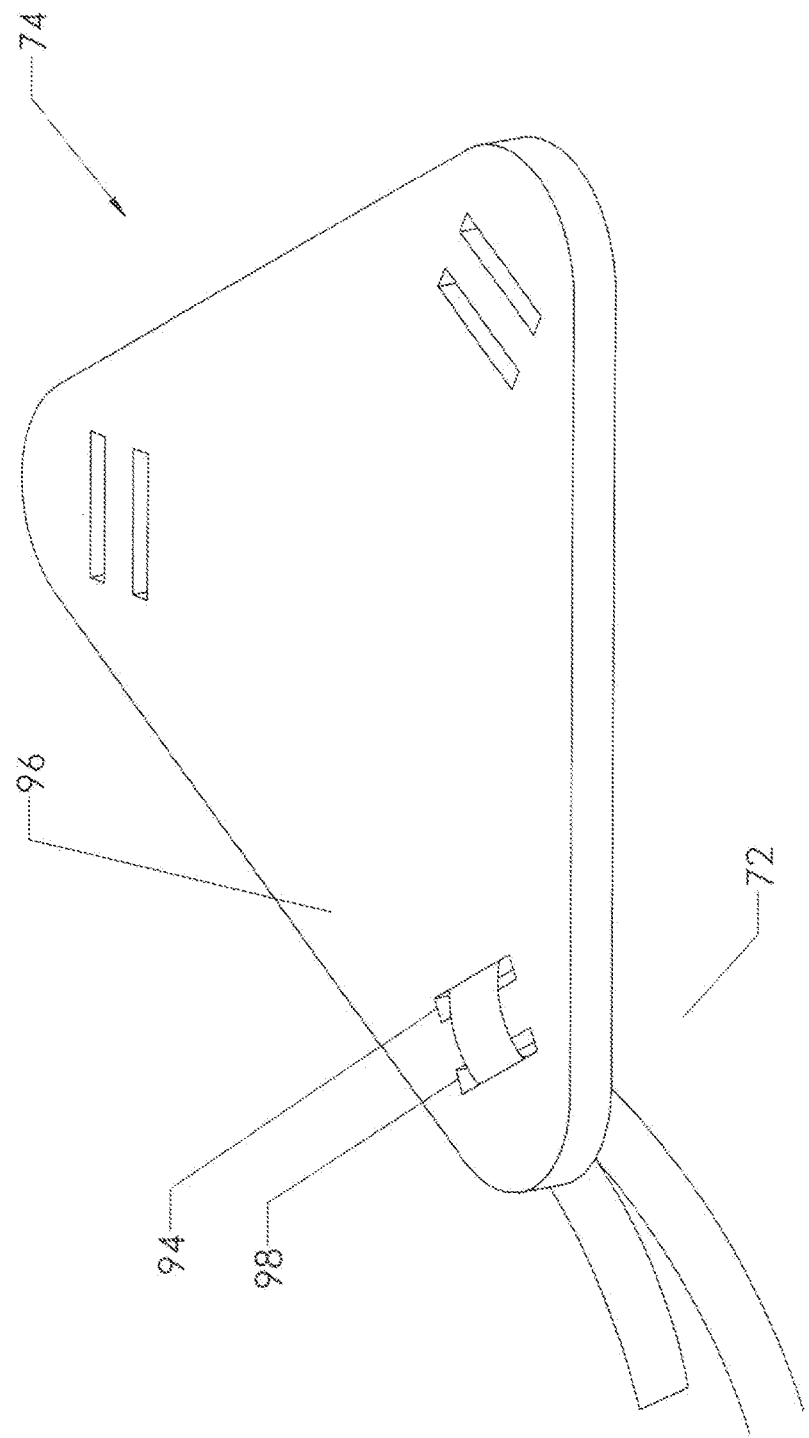
FIG. 16 is a perspective view, showing the coupling of FIG. 15 in more detail.

In order to illustrate the method of attaching straps 72 to coupling 74, coupling 74 is shown in more detail in FIG. 16. In the embodiment depicted strap end 82 (not shown) is inserted upwards through inside coupling slot 94. Strap 72 is then placed over coupling top surface 96. Next, strap 72 is preferably inserted downwards into outside coupling slot 98. When tightened, this fastening method will typically remain locked unless coupling 74 is lifted from the user's head. Lifting coupling 74 will allow the user to loosen strap 72. The fastening method is similar to the method of fastening a backpack. However, in order to ensure straps 72 remain fastened to coupling 74, VELCRO or another temporary method of attaching strap 82 to strap 72 can be used. The details of this are discussed in the preceding text and illustrated in FIG. 13.

Figure 17:
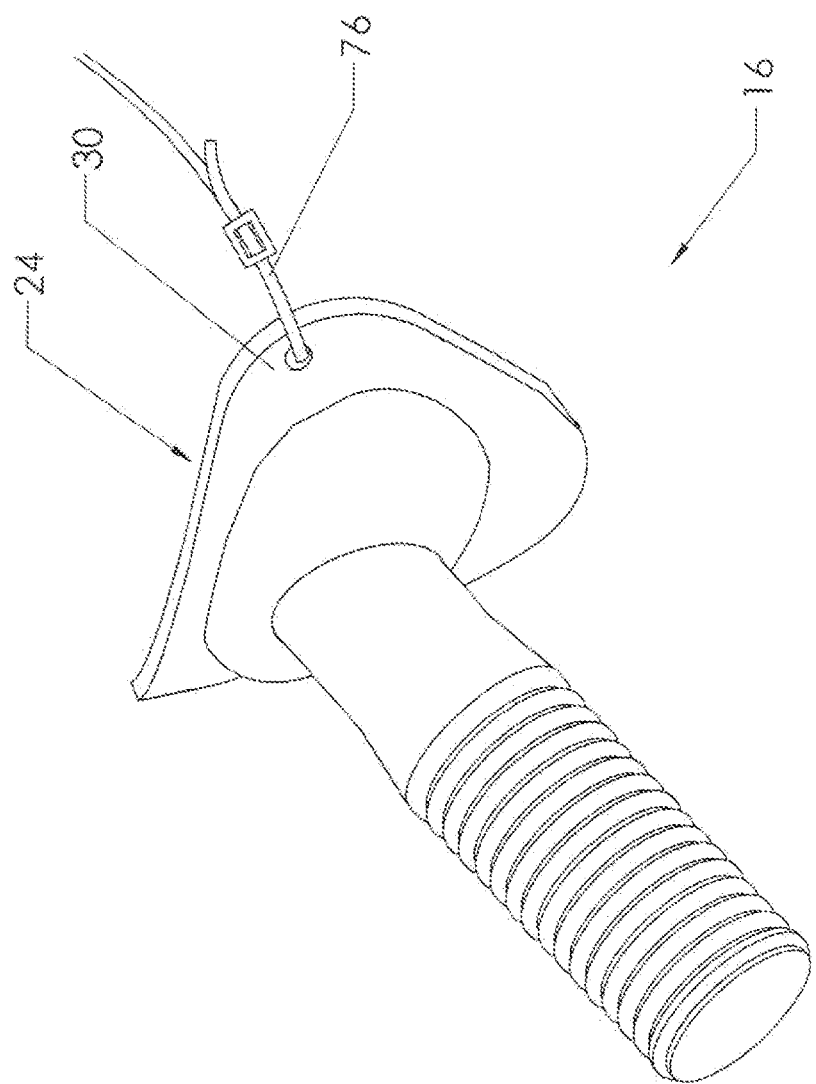
FIG. 17 is a perspective view, showing an alternate type of securing strap.

FIG. 17 shows another embodiment in which the elongate members are omitted and the securing straps are connected directly to the main mask body 24. The balance of the components used is the same for this version.

Figure 18:
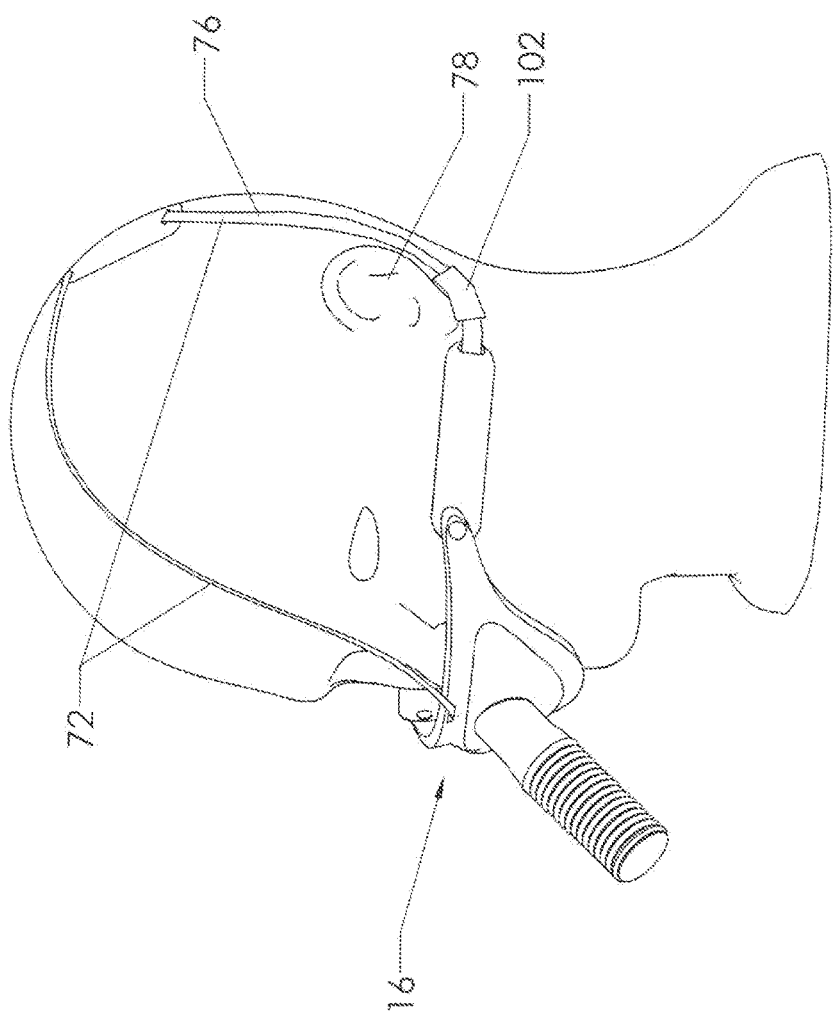
FIG. 18 is a perspective view, showing the addition of a strap cushion wrapped around the strap of the present invention as it passes beneath a user's ear.

FIG. 18 shows still another embodiment in which an enhancement to the strap system is included. Side straps 72 may rub on the lower portions of a user's ear. To reduce this strap cushion 102 is attached to side strap 76, as illustrated. Strap cushion 102 may be made slidable along side strap 72 so that its position may be changed as desired. In addition, strap cushions of various lengths may be provided. Strap cushion 102 is preferably constructed from a soft cotton (or similar) material. Preferably, strap cushion 102 wraps around strap 72. Although strap cushion 102 is shown under the user's ear 78 (a possible location of irritation), strap cushion 102 can be located on the front strap or at any location on the side strap.

Returning to FIGS. 12 and 14, those skilled in the art will realize that the inclusion of elongate member 28 "bridges" the cheekbones and prevents straps 72 from cutting into the user's face as they pass around the convex cheeks and ultimately to the ears. Furthermore, pivot joint 64 allows for self-alignment of elongate member 24 and sides straps 76 as the user affixes mask 16. This preferably results in cushion 52 to settling into a comfortable place on the user's face. The reader will also note that the thickness of cushion 52 (in the preferred embodiment, this is a gel pad) is preferably large enough to prevent side strap 76 from contacting the user's skin. Contact of straps 76 to the user's face could cause irritation.

Figure 19:
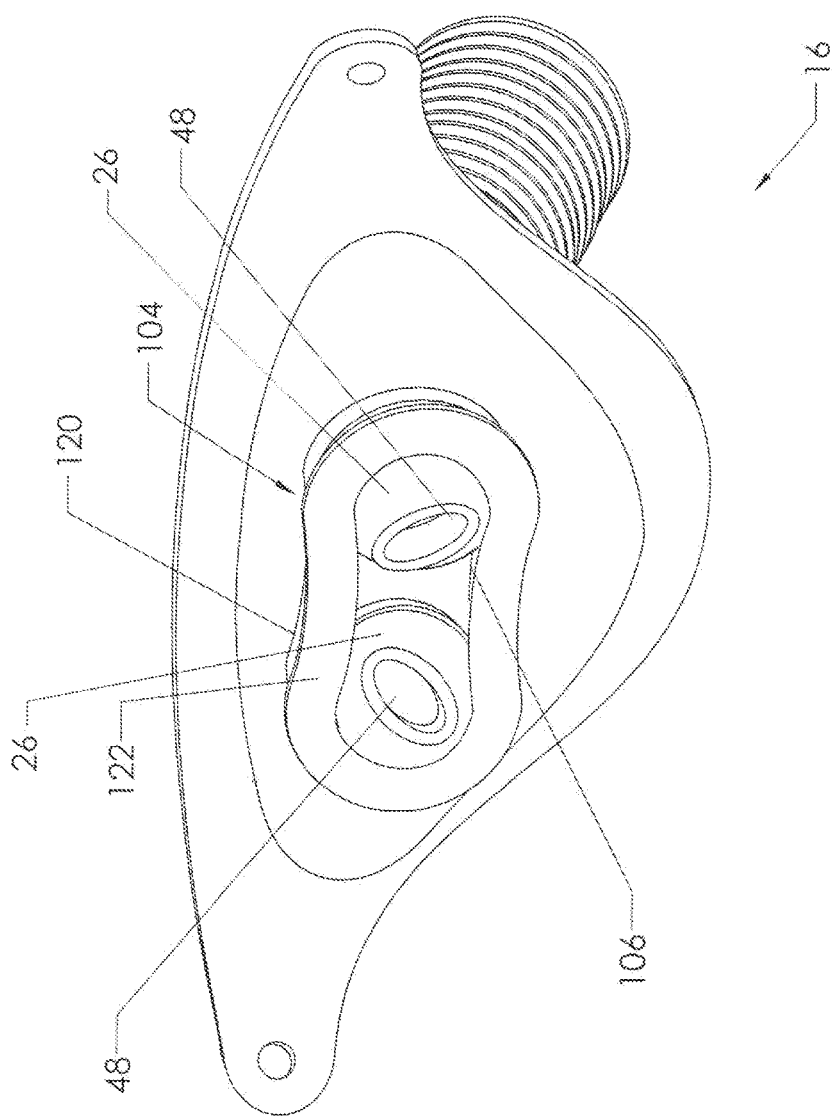
FIG. 19 is a perspective view, showing an embodiment of the present invention in which an additional sealing structure is provided around the nostril-interfacing components.
Figure 20:
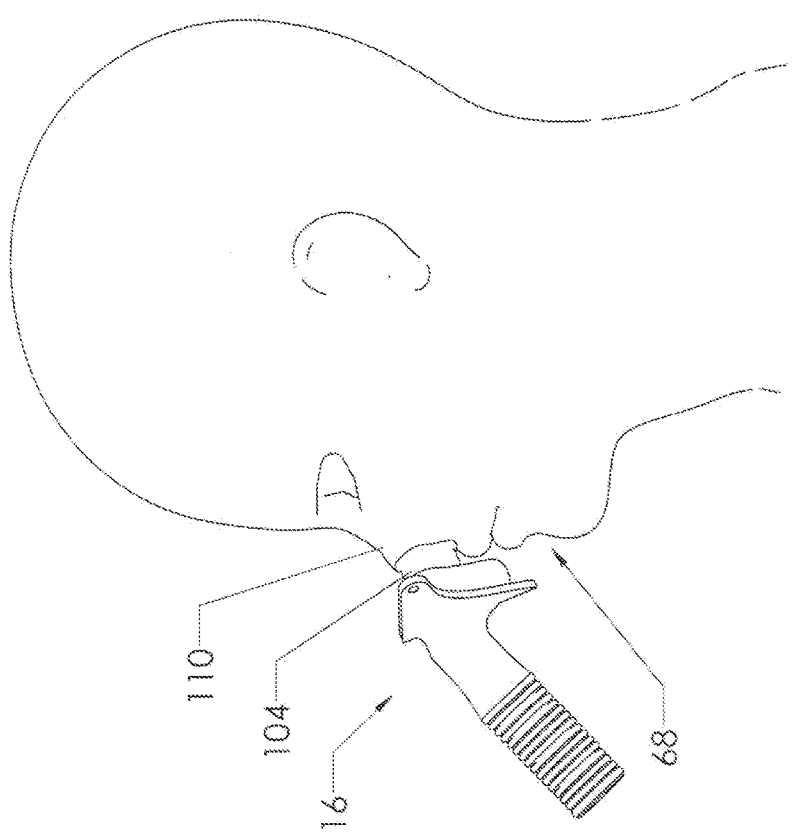
FIG. 20 is an elevation view, showing the inventive mask in position on a user's face.
Figure 21:
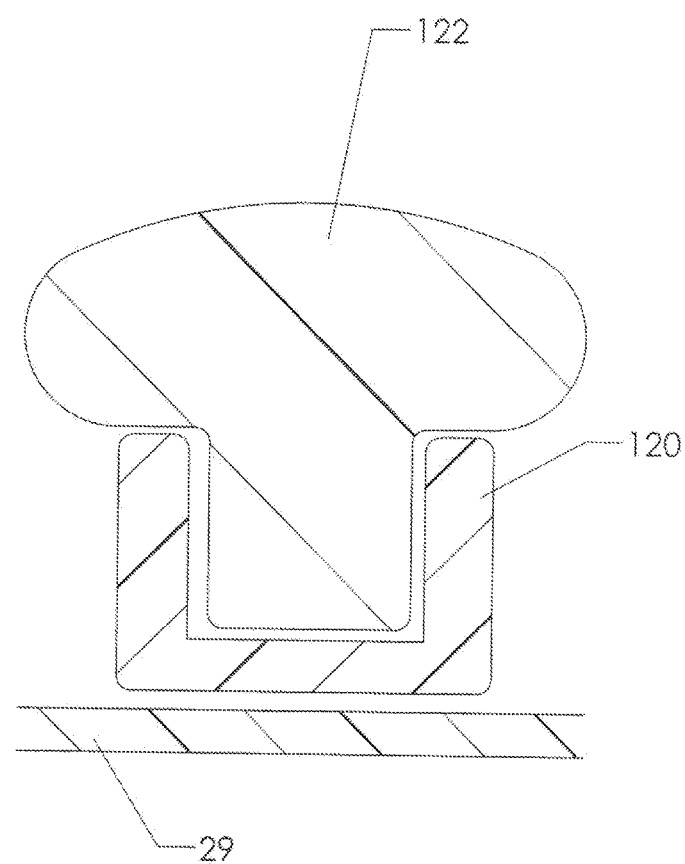
FIG. 21 is a section view, showing details of the sealing structure and how the soft seal is mounted.

The nostril-interfacing components of the embodiment of FIG. 3 (base 29, nostril pillows 26 and nostril inserts 48) are configured to maintain an effective gas seal with the user's nostrils so that positive pressure can be maintained. However, there is such a tremendous variation in human anatomy and individual preferences that it is very difficult for a particular device to work well for everyone. For many users the gas seal is incomplete, and a significant portion of the desired positive pressure leaks from the nostril interface. It is therefore desirable to provide a supplemental or secondary seal that can eliminate or at least reduce this leakage. FIGS. 19-21 show the inclusion of such a secondary seal.

In FIG. 19, the reader will note that sealing structure 104 runs around the two nostril pillows 26 and nostril inserts 48. The sealing structure is configured to form a sealed perimeter to reduce or eliminate pressure leakage from the interface between the two nostril inserts and the user's nostrils. FIG. 21 shows a section through the sealing structure.

Channel 120 is connected to a suitable structure such as base 29 and may in some instances be integrally molded with base 29. The channel contains and locates soft seal 122.

The nature of the material used for soft seal 122 is significant. This material is preferably deformable so that it can contour to the user's face. It is desirable for the material to remain in the deformed state without exerting significant pressure. It is also desirable for the material to be mildly adhesive so that it sticks the to the user's skin and to the channel, thereby forming an effective gas seal. On the other hand, the adhesive properties must be fairly weak so that the soft seal can be pulled free from the user's nose when the mask is removed (without damaging the skin).

Various modeling clays can serve as an effective material for soft seal 122. A foam material contained within an impermeable skin may also be used—such as the material used for the ear cups on aircraft headsets. However, the most effective material presently known to the inventor is a viscoelastic liquid silicone modified by one or more thixotropic agents that help it hold its shape. This class of materials is often referred to as SILLY PUTTY after the amusement product marketed using that name. Various compositions are available. An exemplary composition includes 65% (by mass) dimethyl siloxane, 17% silica, 9% thixatrol ST, 4% polydimethylsiloxane, 1% decamethyl cyclopentasiloxane, 1% glycerine, and 1% titanium dioxide.

A length of this material can be pressed into channel 120 before the user dons the mask. When the mask is tightened the material of soft seal 122 deforms against the users nose and forms a seal. However, once deformed, it does not exert continuous pressure (which can cause numbness and other problems). Instead, it remains in place largely via its deformed shape and adhesion to the skin.

Viscoelastic silicones and similar materials tend to capture skin oils and other contaminants. Thus, the material used for soft seal 122 may need to be discarded and replaced from time to time (such as weekly). The presence of channel 120 makes the replacement operation easy. The user simply peels the old soft seal out and presses a fresh one into place. If a sealed foam is substituted for the clay-like materials, a mild adhesive strip will likely need to be applied to the foam to hold it in position.

FIG. 20 shows gas delivery mask 16 attached to a user's face 68. The reader will note that for the purpose of clarity, all straps and other features of mask 16 have been excluded from the illustration. In the figure, sealing structure 104 forms a perimeter around the user's nostrils. Preferably, the contact between the user's nose 110 and sealing structure 104 prevents gas from traveling up into the eyes and face of the user. Thus, the eyes of the user are not dried out by excessive gas passing over the eyes while the mask 16 is worn.

The preceding description contains significant detail regarding the novel aspects of the present invention. It should not be construed, however, as limiting the scope of the invention but rather as providing illustrations of the preferred embodiments of the invention. As an example, although the design shows the nasal pillow as separate from the main mask body, the design could have the two parts as a single unit. Such variations would not alter the function of the invention. Thus, the scope of the invention should be fixed by the following claims, rather than by the examples given.

Having described my invention, I claim:

1. A gas delivery mask configured to be worn by a user having a head, a left cheek bone, a right cheek bone, a left ear, a right ear, and nostrils, comprising:

a. a main mask body;
b. a first nostril insert and a second nostril insert connected to said main mask body, each of said nostril inserts being configured to deliver gas to said user through said user's nostrils;
c. a channel extending in a single loop around said first and second nostril inserts leaving an open area within said single loop and between said first and second nostril inserts;
d. a removable soft seal placed within said channel, said soft seal comprising a viscoelastic liquid silicone;
e. wherein said removable soft seal forms a loop around said first and second nostril inserts; and
f. a strap assembly configured to secure said main mask body to said user's head.

2. A gas delivery mask as recited in claim 1, further comprising:
a. wherein said main mask body has a first lateral extreme and a second lateral extreme;
b. a first elongate member connected to said first lateral extreme, said first elongate member having a first end and a second end; and
c. a second elongate member connected to said second lateral extreme, said second elongate member having a first end and a second end.

3. A gas delivery mask as recited in claim 2, wherein:
a. said first elongate member includes a cushion configured to extend inward toward said right cheek bone; and
b. said second elongate member includes a cushion configured to extend-inward toward said left cheek bone.

4. A gas deliver mask as recited in claim 2, wherein:
a. said first end of said first elongate member is pivotally connected to said first extreme of said main mask body; and
b. said first end of said second elongate member is pivotally connected to said second extreme of said main mask body.

5. A gas delivery mask as recited in claim 4, wherein:
a. said second end of said first elongate member is connected to a first side strap configured to extend around a first side of said user's head;
b. said second end of said second elongate member is connected to a second side strap configured to extend around a second side of said user's head; and
c. a front strap having a first end and a second end, wherein said first end attaches to said main mask body and a second end configured to extend over said user's head.

6. A gas delivery mask as recited in claim 5, wherein:
a. said first elongate member includes a cushion configured to extend inward toward said right cheek bone; and
b. said second elongate member includes a cushion configured to extend inward toward said left cheek bone.

7. A gas delivery mask as recited in claim 6, further comprising a coupling configured to be located behind said user's head, with said first and second side straps being connected to said coupling.

8. A gas delivery mask as recited in claim 5, further comprising a coupling configured to be located behind said user's head, with said first and second side straps being connected to said coupling.

9. A gas delivery mask as recited in claim 5, further comprising:
a. a first ear strap cushion located on said first side strap; and
b. a second ear strap cushion located on said second side strap.

10. A gas delivery mask as recited in claim 4, wherein:
a. said first elongate member includes a cushion configured to extend inward toward said right cheek bone; and
b. said second elongate member includes a cushion configured to extend inward toward said left cheek bone.

11. A gas delivery mask configured to be worn by a user having a head, a left cheek bone, a right check bone, a left ear, a right ear, and nostrils, comprising:
a. a main mask body;
b. a base connected to said main mask body, said base having a first nostril insert and a second nostril insert, each of said nostril inserts being configured to deliver gas to said user through said user's nostrils;
c. a channel connected to said base and extending in a single loop around said first and second nostril inserts leaving an open area within said single loop and between said first and second nozzle inserts;
d. a removable soft seal placed within said channel, said soft seal including an adhesive surface for selectively adhering said soft seal to said channel;
e. wherein said removable soft seal forms a single loop around both said first nostril insert and said second nostril insert; and
f. a strap assembly configured to secure said main mask body to said user's head.

12. A gas delivery mask as recited in claim 11, further comprising:
a. wherein said main mask body has a first lateral extreme and a second lateral extreme;
b. a first elongate member connected to said first lateral extreme, said first elongate member having a first end and a second end; and
c. a second elongate member connected to said second lateral extreme, said second elongate member having a first end and a second end.

13. A gas delivery mask as recited in claim 12, wherein:
a. said first elongate member includes a cushion configured to extend inward toward said right cheek bone; and
b. said second elongate member includes a cushion configured to extend inward toward said left cheek bone.

14. A gas deliver mask as recited in claim 12, wherein:
a. said first end of said first elongate member is pivotally connected to said first extreme of said main mask body; and
b. said first end of said second elongate member is pivotally connected to said second extreme of said main mask body.

15. A gas delivery mask as recited in claim 14, wherein:
a. said second end of said first elongate member is connected to a first side strap configured to extend around a first side of said user's head;
b. said second end of said second elongate member is connected to a second side strap configured to extend around a second side of said user's head; and
c. a front strap having a first end and a second end, wherein said first end attaches to said main mask body and a second end configured to extend over said user's head.

16. A gas delivery mask as recited in claim 15, wherein:
a. said first elongate member includes a cushion configured to extend inward toward said right cheek bone; and b. said second elongate member includes a cushion configured to extend inward toward said left cheek bone.

17. A gas delivery mask as recited in claim 16, further comprising a coupling configured to be located behind said user's head, with said first and second side straps being connected to said coupling.

18. A gas delivery mask as recited in claim 15, further comprising a coupling configured to be located behind said user's head, with said first and second side straps being connected to said coupling.

19. A gas delivery mask as recited in claim 15, further comprising:
   a. a first ear strap cushion located on said first side strap; and
   b. a second ear strap cushion located on said second side strap.

20. A gas delivery mask as recited in claim 14, wherein:
   a. said first elongate member includes a cushion configured to extend inward toward said right cheek bone; and
   b. said second elongate member includes a cushion configured to extend inward toward said left cheek bone.

\* \* \* \* \*